United States Patent [19]

Berteloot et al.

[11] Patent Number: 5,330,717
[45] Date of Patent: Jul. 19, 1994

[54] ELECTROPNEUMATIC APPARATUS FOR SAMPLING RAPIDLY PREDETERMINED VOLUMES OF A MIXTURE, TO BE CONNECTED TO A COMPUTER

[75] Inventors: Alfred Berteloot, 4652 Boyer, Montreal Quebec, Canada, H2J 3E4; Michel Brunette, Laval, Canada

[73] Assignee: Alfred Berteloot, Montreal, Canada

[21] Appl. No.: 697,769

[22] Filed: May 9, 1991

[51] Int. Cl.$^5$ .................. G01N 21/00; G01N 35/02; G01N 1/14; B01L 3/02
[52] U.S. Cl. ..................... 422/68.1; 422/81; 422/100; 422/110; 436/50; 436/54; 436/55; 436/179; 436/180; 73/863.01; 73/863.02; 73/863.03; 73/864.34; 73/864.35
[58] Field of Search ............ 422/68.1, 81, 82, 100, 422/107, 109, 110, 119; 436/50, 54, 55, 179, 180; 73/863.01, 862.02, 863.03, 864.34–864.35, 864.15, 864.22; 137/209

[56] References Cited

U.S. PATENT DOCUMENTS

| | | | |
|---|---|---|---|
| 3,759,667 | 9/1973 | Bannister et al. | 422/100 |
| 3,990,853 | 11/1976 | Godin | 422/100 |
| 4,204,430 | 5/1980 | Tamm et al. | 73/864.12 |
| 4,427,415 | 1/1984 | Cleveland | 436/57 |
| 4,810,659 | 0/1989 | Higo et al. | 436/180 |

FOREIGN PATENT DOCUMENTS

| | | |
|---|---|---|
| 0938074 | 6/1982 | U.S.S.R. |
| 2033780 | 5/1980 | United Kingdom |
| 2082545 | 3/1982 | United Kingdom |

OTHER PUBLICATIONS

Forbush III, Bliss. "An Apparatus for Rapid Kinetic Analysis of Isotopic Efflux from Membrane Vesicles and of Ligand Dissociation from Membrane Proteins", Analytical Biochemistry, vol. 140 (1984) pp. 494 to 505.
Berteloot et al., "Fast sampling, rapid filtration apparatus: . . . ", Journal of Membrane Biology, vol. 122, Jun. 21, 1991, New York, US. pp. 111-125—A.
B. Chance et al. (Editors) "Rapid Mixing and Sampling Techniques in Biochemistry" 1964, Academic Press, New York, N.Y., US pp. 289-301, R. H. Eisenhardt.
B. Chance et al. (Editors) "Rapid Mixing and Sampling Techniques in Biochemistry" 1964, Academic Press, New York, US pp. 275-287, K. K. Lonberg-Holm.

Primary Examiner—Robert J. Warden
Assistant Examiner—Christopher Y. Kim
Attorney, Agent, or Firm—Collard & Roe

[57] ABSTRACT

An electropneumatic apparatus for sampling rapidly predetermined volumes of a mixture, to be connected to a computer. It comprises an injector provided with a detector connected to the computer for indicating activation of the injector; a reactor having a chamber provided with at least one aperture, the chamber being provided in its superior portion with an air inlet/outlet connected to a pressurized air system, the chamber having a bottom outlet provided with a flow sensor connected to the computer for indicating a volume of fluid exiting from the bottom outlet; the pressurized air system having an air channel provided with a first portion connected to an air source, and a second portion connected to the air inlet/outlet of the chamber, the air channel being provided with an air controlling device connected to the computer for producing a succession of positive and negative pressures inside the chamber, whereby the predetermined volumes of the mixture can be sampled from the bottom outlet under control of the computer; and a receiving system comprising a mobile manifold array for receiving successive samples exiting from the bottom outlet of the chamber.

9 Claims, 5 Drawing Sheets

ELECTROPNEUMATIC APPARATUS FOR SAMPLING RAPIDLY PREDETERMINED VOLUMES OF A MIXTURE, TO BE CONNECTED TO A COMPUTER

FIELD OF THE INVENTION

The present invention relates to an electropneumatic apparatus and a method for sampling rapidly predetermined volumes of a mixture.

More particularly, the present invention relates to chemistry and biology applications.

BACKGROUND OF THE INVENTION

Known in the art, there is the U.S. Pat. No. 4,836,244 granted on Jun. 6, 1989. In this patent, there is described a device for supplying constant pressure to a microcapillary to carry out process of controlling injection of small fluid samples through the microcapillary. The device comprises a main line connected to the microcapillary, a pressure source, and a valve system by which different positive pressures are produced inside the microcapillary. One drawback with the present apparatus is that no means is provided for mixing different reagents to produce a mixture, and no means is provided for rapidly sampling this mixture.

Also known in the art, there is U.S. Pat. No. 4,454,032 granted on Jun. 12, 1984. In this patent, there is described a fast filtering apparatus comprising an injection device, a filter supporting device, and a device for ensuring a fast and temporary contacting of the injection device and the filter support device. The fast filtering process is controlled by an electronic control means. Again, one drawback with the present invention is that no means is provided for mixing different reagents to produce a mixture, and no means is provided for rapidly sampling this mixture.

Also known in the art, there are the following patents: U.S. Pat. No. 4,427,415, "MANIFOLD VACUUM BIOCHEMICAL TEST METHOD AND DEVICE" Patrick H Cleveland; U.S. Pat. No. 4,415,449, "VACUUM FILTRATION BENCH", Wolfgang Hein, Carl Schleicher, GmbH & Co. KG; U.S. Pat. No. 3,888,770, "PLURAL-SAMPLE FILTER DEVICE" Shlomo Avital et al.; U.S. Pat. No. 3,730,352, "FILTRATION APPARATUS", Stanley N. Cohen et al., New Brunswick Scientific Co. Inc.; and U.S. Pat. No. 3,319,792, "MULTIPLE FILTRATION APPARATUS", Philip Leder et al., U.S.A. Department of Health, Education and Welfare.

None of the above patents provides a means for rapidly sampling a mixture.

It is an object of the present invention to provide an apparatus and a method for mixing different reagents to produce a mixture, and for rapidly sampling this mixture.

SUMMARY OF THE INVENTION

According to the present invention, there is provided an electropneumatic apparatus for sampling rapidly predetermined volumes of a mixture, to be connected to signal processing and controlling means, comprising:

an injector for injecting a first reagent, said injector being provided with a detector to be connected to said processing and controlling means for indicating activation of said injector;

a reactor having a chamber provided with at least one aperture for receiving the first reagent from said injector, and a second reagent for producing said mixture, said chamber being provided in its superior portion with an air inlet/outlet means to be connected to a pressurized air system, said chamber having a bottom outlet provided with a flow sensor to be connected to said processing and controlling means for indicating a volume of fluid exiting from said bottom outlet;

said pressurized air system having an air channel provided with a first portion to be connected to an air source, and a second portion connected to the air inlet/outlet means of said chamber, said air channel being provided with air controlling means connected to said processing and controlling means for producing a succession of positive and negative pressures inside said chamber whereby said predetermined volumes of said mixture can be sampled from said bottom outlet under control of said processing and controlling means; and a receiving system comprising a mobile manifold array for receiving successive samples of said mixture exiting from the bottom outlet of said chamber, and a motor controlled by said processing and controlling means, for moving said manifold array to receive said successive samples.

According to the present invention, there is also provided a method for performing a fast sampling of a liquid mixture contained in a chamber, said chamber having a bottom aperture provided with a flow sensor connected to processing and controlling means, and an upper aperture disposed in a superior portion of said chamber, said upper aperture being connected to a pressurized air system capable of producing alternately positive and negative pressures inside said chamber, said liquid mixture being held inside said chamber by a negative pressure produced by said air system, said air system being controlled by said processing and controlling means, said method comprising steps of:

producing a succession of negative and positive pressures inside said chamber by means of said pressurized air system controlled by said processing and controlling means, for exiting predetermined sample volumes from said bottom aperture, said processing and controlling means calculating said predetermined sample volumes by means of said flow sensor; and moving a manifold array under said bottom outlet for collecting said predetermined sample volumes, said manifold array being moved by means of a motor controlled by said processing and controlling means.

The objects, advantages and other features of the present invention will become more apparent upon reading of the following non-restrictive description of a preferred embodiment thereof, given for the purpose of exemplification only, with reference to the accompanying drawings.

DETAILED DESCRIPTION OF A PREFERRED EMBODIMENT

Figure 1:
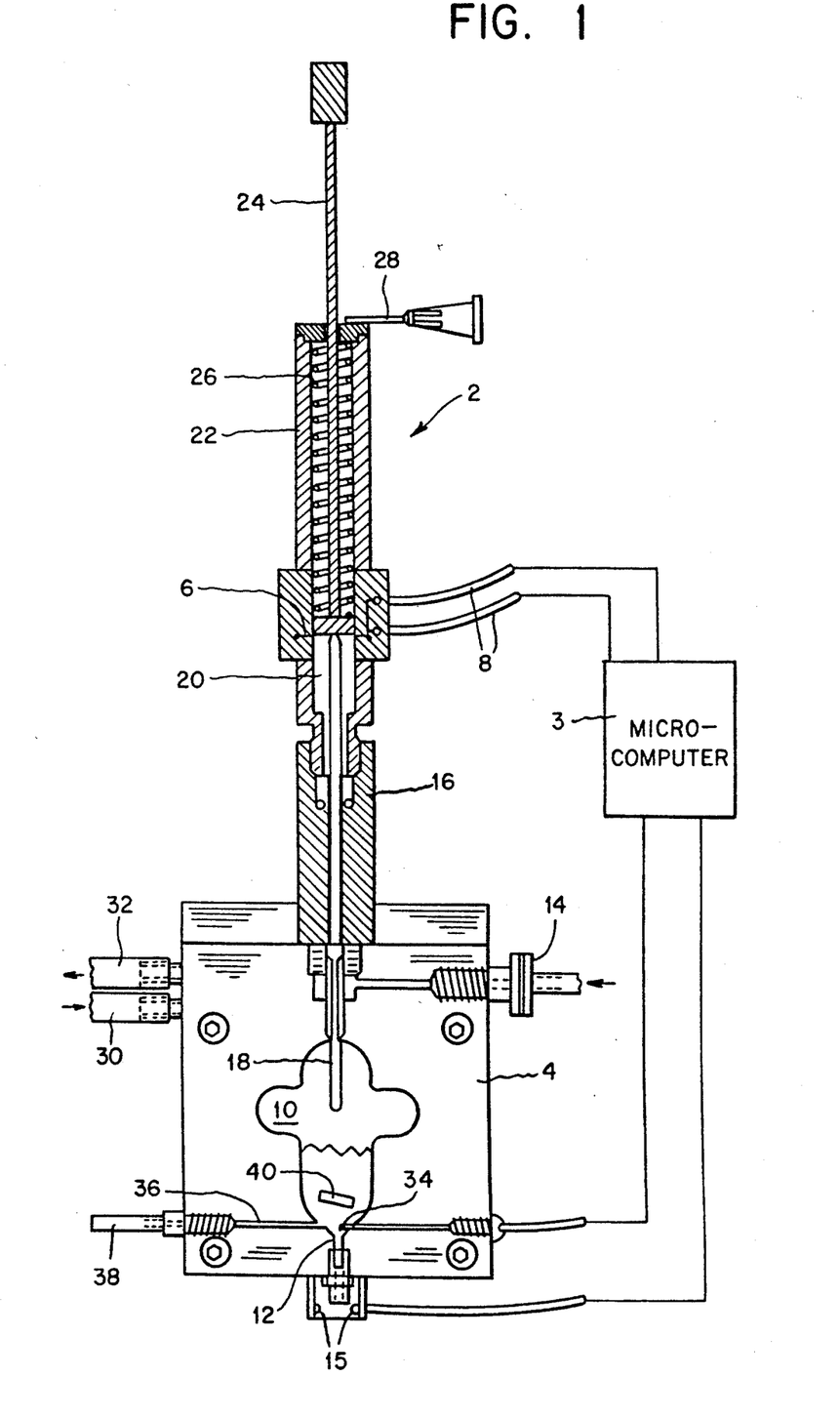
FIG. 1 is a side partial cross section view of an injector and a reactor of an apparatus according to the present invention.

Referring now to FIG. 1, there is shown the injector and the reactor of an electropneumatic apparatus for sampling rapidly predetermined volumes of a mixture. This apparatus is connected to a computer 3 provided with appropriate interfaces. The apparatus comprises an injector 2 for injecting a first reagent into the reactor 4. The injector is provided with a detector switch 6 connected to the computer 3 by means of wires 8 for indicating activation of the injector 2. The reactor 4 has a chamber 10 provided with an aperture for receiving the first reagent from the injector 2. The reactor 4 can receive the second reagent by its bottom aperture 12 by creating a negative pressure inside the chamber 10. The process for creating this negative pressure will be explained later on. By mixing the first reagent and the second reagent, a mixture is produced inside the chamber 10. The chamber 10 is provided in its superior portion with an air inlet/outlet 14 that is connected to a pressurized air system (not shown in this figure). The chamber 10 has the bottom outlet 12 which is provided with a flow sensor 15. This flow sensor 15 is connected to the computer 3 for indicating a volume of fluid exiting from said bottom outlet 12.

The injector 2 comprises a pipette holder 16 mounted on top of the reactor 4, for holding a pipette 18 containing the first reagent. The injector 2 also comprises a rod 20 having an end inserted into the pipette 18 for ejecting the first reagent out of the pipette 18 by driving the rod 20 into the pipette 18. A piston device is provided. It is mounted on top of the pipette holder 16. This piston device includes a piston cylinder 22, a piston 24 disposed inside the cylinder 22, and a return spring 26 for biassing the piston 24 toward the rod 20. A pin 28 is provided for locking the piston 24 in a position where the return spring 26 is compressed, whereby a user can activate the injector 2 to eject the first reagent out of the pipette 18 into the reactor 4 by removing the pin 28.

The reactor 4 comprises a first channel having inlet 30 and outlet 32 connected to a thermoregulating system (not shown) controlled by the computer, whereby a thermoregulating fluid can be injected into the first channel for regulating the temperature of the mixture inside the chamber 10. A probe 34 is disposed in the bottom portion of the chamber 10 and connected to the computer 3 for monitoring the temperature of the mixture in the chamber 10.

A second channel 36 is provided for linking the bottom portion of the chamber 10 to, an inlet/outlet 38 of the reactor 4. This inlet/outlet 36 is connected to a washing system (not shown in this figure) for alternately entering or exiting a washing fluid to and from the chamber 10. The chamber 10 is characterized by having a cruciform shape. Also, a magnetic mixing element 40 is provided for mixing the mixture inside the chamber 10.

Figure 2:
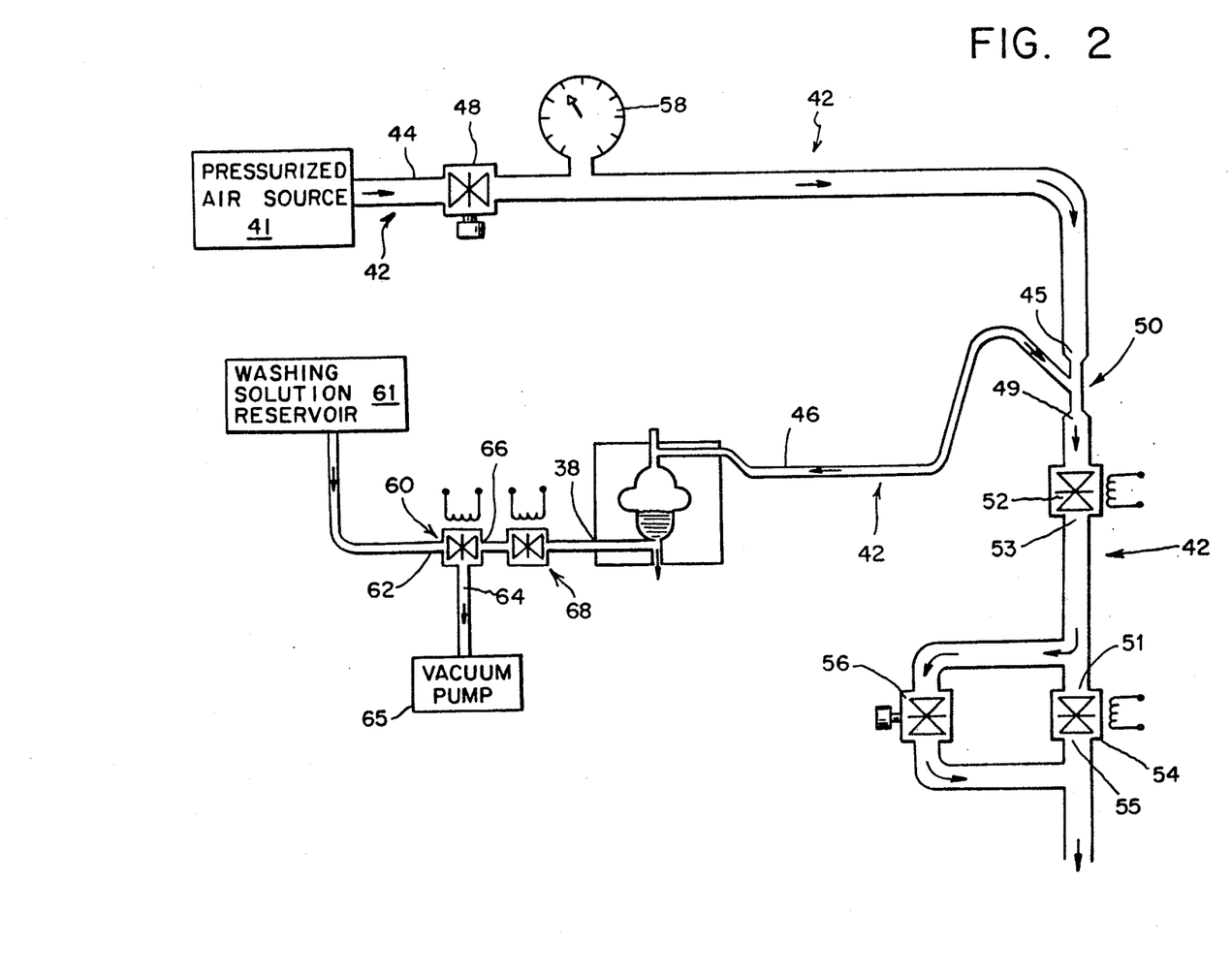
FIG. 2 is a schematic diagram illustrating a pressurized air system of the apparatus according to the present invention.

Referring now to FIG. 2, there is shown the pressurized air system of the present electropneumatic apparatus. This system has an air channel 42 provided with a first portion 44 connected to a pressurized air source 41, and a second portion 46 connected to the air inlet/outlet 14 (shown in FIG. 1) of the chamber 10. The air channel 42 is provided with several valves 52 and 54 controlled by the computer for producing a succession of positive and negative pressures inside the chamber 10, whereby predetermined volumes of the mixture can be sampled from the bottom outlet 12 under control of the computer.

The second portion 46 of the air channel 42 has a reduced diameter with respect to the diameter of the first portion 44. A first manual regulating valve 48 is disposed along the first portion 44. A venturi 50 is provided. It has an inlet 45 connected to the first portion 44 of the channel 42, an inlet/outlet middle aperture connected to the second portion 46, and an outlet 49. There is also a first impulsion valve 52 controlled by the computer. It has an end connected to the outlet 49 of the venturi 50. The second impulsion valve 54 is also controlled by the computer. It has an end 51 connected to the other end 53 of the first impulsion valve 52, and another end 55 connected to ambient atmosphere. A second manual regulating valve 56 is connected in parallel to the second impulsion valve 54. A manometer 58 is disposed along the first portion 44.

The first manual valve 4 8 can be used by a user for regulating air pressure inside the air channel 42. The second manual valve 56 is used for producing a negative pressure inside the chamber 10. The first impulsion valve 52 is controlled by the computer for producing a succession of negative and positive pressures inside the chamber 10 by which a fast sampling of the predetermined volumes can be done. The second impulsion valve 54 is controlled by the computer for producing a negative pressure inside the chamber 10 during a certain time period after that a positive pressure is produced inside the chamber 10 to reestablish as fast as possible the following negative pressure inside the chamber 10.

Also shown in this FIG. 2, there is the washing system. This system comprises a three-way valve 60 controlled by the computer. This valve 60 has a normally closed inlet 62 connected to a washing fluid source 61, a normally open outlet 64 connected to a vacuum pump 65, and an inlet/outlet 66. A second valve 68 is also provided. It is controlled by the computer. This second valve 68 has first inlet/outlet connected to the inlet/outlet 66 of the first valve 60. The second inlet/outlet of the valve 68 is connected to the inlet/outlet 38 of the reactor 4. A washing fluid is sent into the chamber 10 when the first and second valves 60 and 68 are activated. Then, the fluid inside the chamber 10 is sucked by means of the vacuum pump 65 when only the first valve 60 is activated. No washing operation is performed on the chamber 10 when the first and second valves 60 and 68 are not activated.

Figure 3:
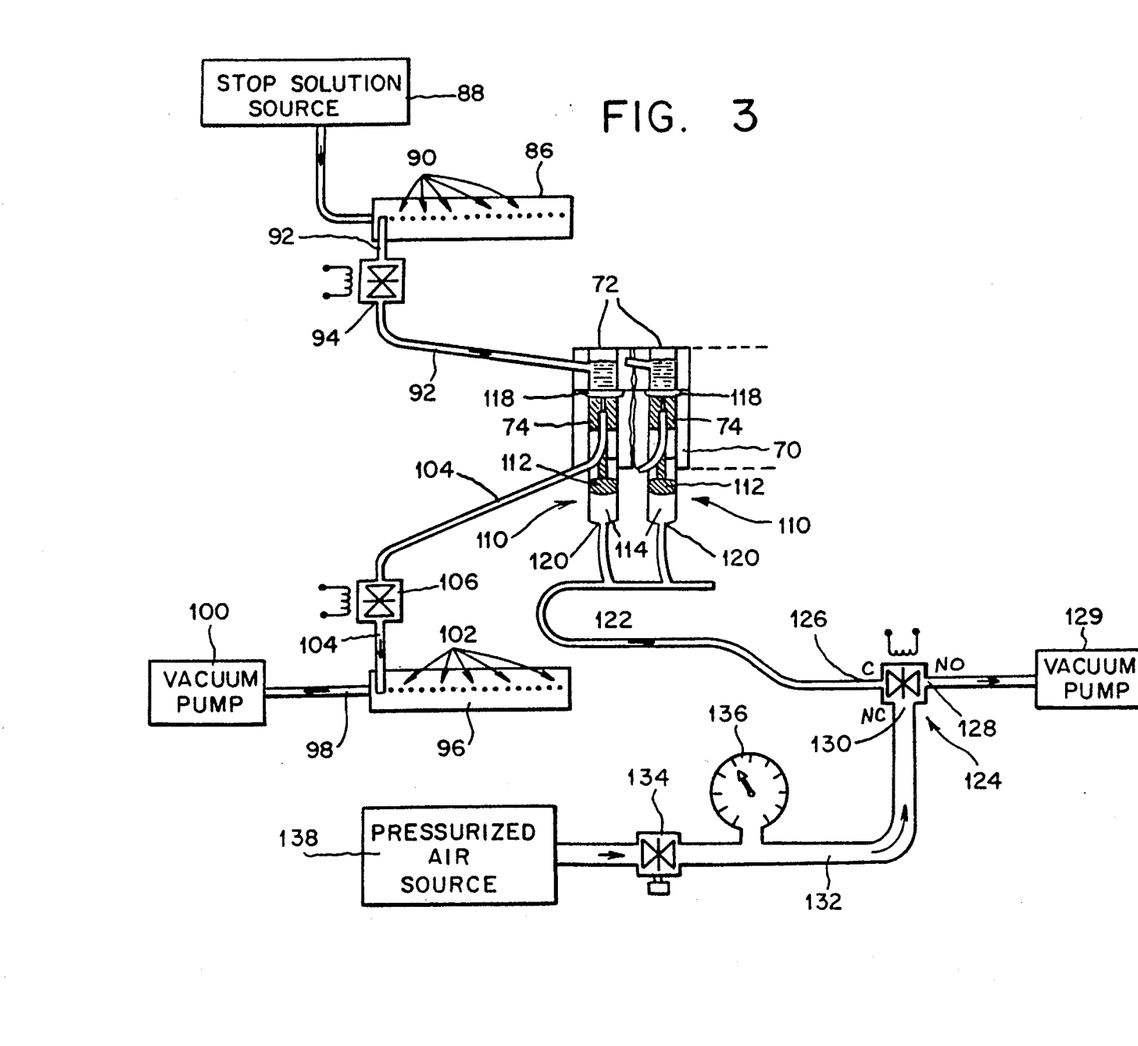
FIG. 3 is a schematic diagram illustrating a receiving system of the apparatus according to the present invention.

Referring now to FIG. 3, there is shown the receiving system of the present electropneumatic apparatus. This receiving system comprises a mobile manifold array 70 for receiving successive samples of the mixture exiting from the bottom outlet 12 of the chamber 10. A motor (not shown) controlled by the computer is provided for moving the manifold array 70 to receive the successive samples while they are exiting from the bottom outlet 12.

Figure 4:
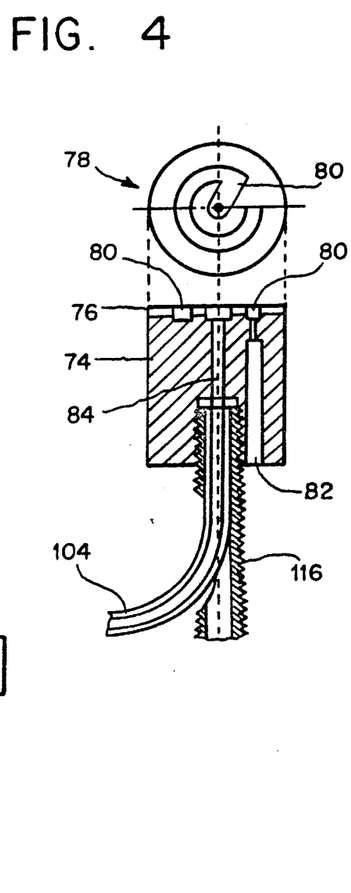
FIG. 4 illustrates in cross section view one of the holding members shown on FIG. 3, and in a view from above, the superior surface of this holding member.

Referring now to FIGS. 3 and 4, the manifold array 70 comprises an array of reservoirs 72 for receiving each of the predetermined volumes of the mixture from the bottom outlet 12 of the chamber 10. Only two reservoirs 72 are shown in FIG. 3, but several reservoirs are normally provided. A filter holder system is provided for supporting a filter 76 in the bottom of each reservoir 72. The filter holder system has a plurality of holding members 74 forming respectively the bottom of each of the reservoirs 72. Each of the holding members 74 has a filter seat 78 provided with a concentric groove 80 for increasing filtering rate. An air channel 82 is provided for connecting the filter seat 78 of the holding member 74 with its bottom surface to ensure complete removal of liquid from the groove 80 at the end of filtering. A channel outlet 84 is provided for draining the upper reservoir 72.

Referring now more specifically to FIG. 3, the receiving system comprises a stop solution system having a manifold array 86 provided with an inlet connected to a stop solution source 88, and a plurality of outlets 90 connected to corresponding tubes 92 having each one a valve 94 controlled by the computer. The tubes 92 are connected to corresponding reservoirs 72 of the mobile manifold array 70. Please note that only one tube 92 and only one valve 94 is shown in this FIG. 3, but each of the outlets 90 is provided with such tube 92 and valve 94.

The receiving system also comprises a collecting system having a manifold array 96 provided with an outlet 98 connected to a vacuum pump 100, and a plurality of inlets 102 connected to corresponding tubes 104 having each a valve 106 controlled by the computer. The tubes 104 of the collecting system are connected respectively to the channel outlets 84 of the holding members 74. Please note that only one tube 104 and only one valve 106 is shown in this FIG. 3, but it has to be appreciated that each inlet 102 is provided with such tube 104 and valve 106.

The present electropneumatic apparatus further comprises a pneumatic system having piston cylinder assemblies 110 having a piston 112 and a cylinder 114 into which the piston 112 is slidably mounted. Each of the piston cylinder assemblies 110 has a channel providing a passageway for the corresponding tubing 104 of the collecting system. Each of the pistons 112 has an upper portion 116 connected to the corresponding holding member 74 and an air-tight lower portion slidebly mounted into the corresponding cylinder 114. Each of the cylinders 114 has a side aperture 118 for positioning a filter 76 on the corresponding holding member 74 when its corresponding piston is down. Each of the cylinders is also provided with a bottom aperture 120. A tubing 122 is connected to the bottom aperture 120 of each of the cylinders 114.

The three-way valve 124 is controlled by the computer. It has an inlet 126 connected to the tubing 122, a normally open outlet 128 connected to vacuum pump 129, and a normally closed outlet 130 connected to a pressurized air channel 132 provided with a regulator 134 and a manometer 136. The pressurized air channel 132 is connected to a pressurized air source 138. The tubing 122 of the pneumatic system is linked to the vacuum pump 129 to bring the pistons 112 down when the three-way valve 124 is not activated by the computer, and the tubing 122 of the pneumatic system is linked to the pressurized air source 138 to lift the pistons in an operative position when the three-way valve 124 is activated by the computer.

According to the present invention, there is provided a method for performing fast sampling of a liquid mixture contained in the chamber 10. The chamber 10 has a bottom aperture 12 provided with a flow sensor 15 connected to the computer 3, and an upper aperture disposed in a superior portion of the chamber 10. The upper aperture is connected to a pressurized air system capable of producing alternately positive and negative pressures inside the chamber 10. The liquid mixture is held inside the chamber 10 by a negative pressure produced by the air system. The air system is controlled by the computer. The method comprises steps of producing a succession of negative and positive pressures inside the chamber 10 by means of the pressurized air system controlled by the computer, for exiting predetermined sample volumes from the bottom aperture 12, the computer calculating the predetermined sample volumes by means of the flow sensor 15; and moving the manifold array 70 under the bottom outlet 12 for collecting the predetermined sample volumes, the manifold array being moved by means of a motor controlled by the computer.

The main components of the apparatus are as follows: a recirculating water bath, a thermoprobe, a regulator, a manometer, a venturi, an impulsion valve, a pressure valve, other valves, a stepping motor, Teflon (trade mark) 0-rings, polyethylene tubings, disposable pipette tips, and a vacuum pump having the following characteristics: $\frac{1}{3}$ HP, 1725 RPM and 29 inches of mercury pressure.

The main parts of the apparatus consist of a vesicle injector 2 which is mounted on top of an incubation chamber 10 thermoregulated through a connection with a recirculating water bath. Vesicles constituting the first reagent can be loaded easily into the injector 2 which is simply screwed to the incubation chamber 10. A gentle suction controlled by a valve 56 allows the loading of the incubation medium constituting the second reagent into the incubation chamber 10 through the opening 12 in its bottom part. Samples are recovered in a manifold array 70 made of eighteen individual filter holder units with their own system of filtering and washing. The filters 76 are easily loaded and unloaded from their respective holders since both up (working) and down (resting) positions are available. The stop solution (in general 1 ml) contained in bottle 88 (usually kept on ice) can be automatically delivered to the upper reservoir 72 of the filter holder units such as to be ready to receive the vesicle samples and efficiently and rapidly stop the reaction. The manifold array 70 shuttles below the incubation chamber 10 according to a predetermined time sequence and allows for fast sample recuperation. During the washing and filtering procedures, a predetermined sequence of filling the upper reservoir with stop solution and filtering is performed. At the end of a run, the chamber 10 can be semiautomatically washed out with deionized water using valves 60 and 68.

The inside of the main body of the apparatus contains all the valves, manifolds, tubings, and electronics which compose the different circuits involved in the control of the functioning of the chamber 10 and the manifold array 70. It also contains a home made microcomputer which controls the synchronisation of the sequences required for injection, mixing, sampling, washing, and filtering. This computer is connected to a standard microcomputer 3 which allows for easy communication between the experimenter and the apparatus. Actually, all of the parameters which can be modified are easily keyed in computer and visualized on monitor. To run the apparatus, all that is needed is an air pressure system (the working pressure being controlled by manometer), a vacuum pump, and, of course, electricity.

A magnified view of the vesicle injector 2 mounted on top of the incubation reactor 4 is shown on FIG. 1. As can be viewed from that figure, the injector per se is composed of a plastic bottom part which just serves as a pipette holder 16 and can be screwed in and out of the incubation reactor 4. The upper part of the vesicle injector 2 screwed on the plastic bottom part, contains a home made, spring-activated piston system which is manually compressed and held in this position by pin 28. Injection of the vesicles starts by manually removing pin 28. The whole sequence of mixing, sampling, filtration and washing is then triggered by an electric signal generated on wires 8, which is activated along the down run of the piston 24 and sent to the machine microcomputer 3. This device allows for a very precise recording of the zero time. A direct estimate of the time required for the injection was performed using two electrodes, one in the chamber and the other one sensing the signal of the piston. It was thus found that not more than 5 ms are required for this step.

The incubation reactor 4 is made of plexiglass and is mounted on a hollow brass block which is connected through inlet 30 and outlet 32 to a recirculating water bath. This allows for temperature control of the transport reaction from 5° to 45° C. Since the heat exchange between brass and plastic is not particularly good and since the water bath is not very close to the incubation chamber 10, the real temperature of the reaction mixture had to be monitored from the inside of the chamber 10, by using a thermoprobe 34. This thermoprobe 34 was calibrated against a range of precisely determined temperatures and the standard curve was introduced into the computer. Since the thermoprobe 34 is permanently coupled to the two computers, the temperature in °C. can be read at any time from the monitor.

As can be seen from FIG. 1, we had to specifically design the inside shape of the incubation chamber 10. As will be discussed later, the functioning of the chamber relies on an alternation between inside negative and positive pressures such as to allow for fast sampling. Moreover, in the earlier versions of the chamber 10, continuous bubbling had to be maintained to keep the incubation mixture from leaking out, which resulted sometimes in foaming with the formation of bubbles in a round shaped chamber and would contaminate the air circuit. Hence, a cruciform design which allows for bubbling without those problems was elaborated. It should be noted that bubbling has now been reduced to a minimum but that this shape is still very convenient, since it serves to increase the inside air volume. As such, liquid is restricted to the bottom part of the chamber 10 with a maximum volume of 1 ml. This part also contains the magnetic stirrer 40 which is activated by a magnetic motor (not shown), placed behind the chamber 10. The magnetic stirrer 40 is automatically activated from the start signal and its action is automatically interrupted 100 ms following activation of a signal, in order to minimize foaming of the vesicle suspension and any interference with the sampling sequence. It appears that complete mixing must occur during this time, since initial linearities in uptakes are always observed. It should be noted in this context that this step does not appear crucial, since a very small volume of vesicles (10 to 40 $\mu$l) is forcibly injected into a much larger volume (0.25 to 1 ml) and thus, by itself, the injection already allows for a good dispersion of the vesicles into the incubation medium.

It should be noted from FIG. 1 that the chamber 10 is permanently open to the exterior through a small needle screwed in its bottom part. Such a system was found most useful, since it avoided the necessity for the in and out control of liquid flow through any kind of valve or mobile systems, our early attempts with these having proved very frustrating. In these conditions, it is thus obvious that we had to design a special system that would allow for liquid retention inside the chamber while allowing for fast sampling of aliquots, a problem which was solved by using the air pressure/vacuum system to be now described.

The upper part of the incubation chamber 10 is connected to an air pressure system (shown in FIG. 2), which controls both the loading of the incubation medium into the chamber 10 and the sampling of aliquots from the vesicle mixture into the manifold array 70. This circuit is shown in FIG. 2, where the incubation chamber 10 has been schematized. The 15 chamber 10 is directly connected to a venturi 50 in which compressed air (10 to 40 psi) is allowed to flow under the control of a regulator 48 connected to manometer 58. When flowing in the principal circuit (one way arrows), the compressed air establishes a vacuum in the branch of the venturi 50 which is connected to the chamber 10 (double arrows). Thus control of air flow through the valve 56 allows for control of the negative pressure inside the chamber 10. Loading of the incubation medium inside the chamber 10 can thus be performed with the valve 56 which increases the vacuum in the chamber 10. The incubation medium of desired composition and preset volume (from 0.25 to 1 ml) can thus be aspirated inside the chamber 10 in a quantitative way using a small polyethylene tubing inserted on the bottom opening of the chamber. The valve 56 is then turned down such as to keep the minimum negative pressure inside the chamber 10 which is necessary for preventing the medium from falling out. The sensitivity of the system is now such that constant bubbling is not necessary for performing this task.

The same circuit is also used for sampling from the incubation chamber 10, since blocking the air flow in the principal circuit by the impulsion valve 52 transforms the negative pressure inside the chamber 10 into a positive one, thus forcing some liquid out of the chamber 10. The sampling volume can therefore be controlled by the closing time of the impulsion valve 52 and by the pressure applied to the main circuit. Immediately after the reopening of the valve 52, the impulsion valve 54 is now triggered and fully opens the main circuit for a short predetermined time (10 ms), thus allowing for a maximum vacuum inside the chamber 10. This maneuver minimizes the dead time of the apparatus, since the circuit can regain its initial state faster.

Obviously, the air pressure system which controls the functioning of the sampling process does not allow for preset volumes to be determined. This problem was solved by using a photoelectric cell 15 which is placed at the very exit of the incubation chamber 10 and allows for measurement of the sampling duration.

Figure 5:
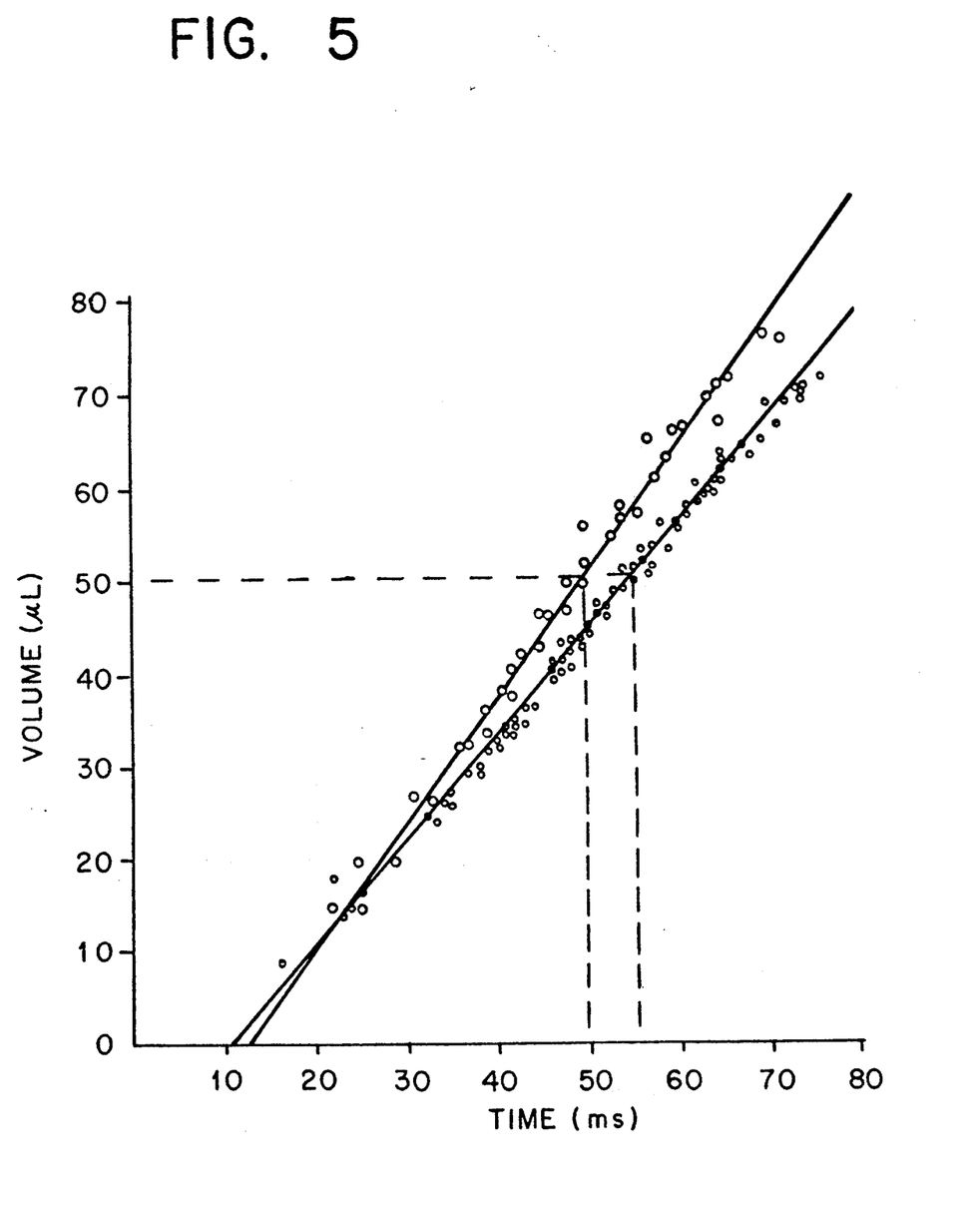
FIG. 5 is a diagram illustrating sampling volume versus sampling duration, to show a calibration curve.

The sampling volume can now be estimated from a calibration curve which was performed as follows. A pyranine solution of known concentration was introduced into the incubation chamber 10 and a precisely measured volume of 1 ml water was placed into the upper reservoir 72 of the manifold array 70. All filtration and washing circuits were deactivated so that, with this set up, the filters 76 introduced in each filter holder unit served only to prevent leakage of liquid. The sampling process was then initiated and, after completion of the run, the content of each recuperation unit was thoroughly mixed, using an automatic pipette and several pumping in and out. An aliquot of 900 μl was then manually extracted from each reservoir and the pyranine concentration measured in a spectrophotometer at a wavelength of 454 nm. The resulting calibration curve, as obtained using different pressures (15 to 25 psi) in the main air circuit and different closing times (12 to 30 ms) for the valve 52, is shown in FIG. 5 (solid symbols). These results demonstrate a very good linear relationship ($r=0.991$) between the sampling volume (15 to 90 μl) and the sampling duration (20 to 80 ms) under all sets of conditions. Extrapolation of this straight line to the time axis shows an intercept of 11 ms, which actually corresponds to the minimum time required to go from inside negative to inside positive pressure in the chamber after closing of the valve 52, and thus represents the inertia of the air pressure system. Similar results were obtained using a mixture of membrane vesicles and pyranine inside the incubation chamber, FIG. 5, open symbols. In that case, the extrapolated intercept on the time axis (12.5 ms) of the linear relationship ($r=0.993$) is entirely compatible with the dead time determined in the absence of vesicles. However, a slight increase in the slope value as compared to the situation in the absence of vesicles was found, a quite logical finding when considering the difference in medium viscosity between these two situations.

Our working conditions in the presence of vesicles were thus set in the middle range of the time/volume relationship, using 15 psi in the main air circuit and 18 ms closing time for valve 52. Under these conditions, the reproducibility of the sampling process was estimated from the sampling durations on 8 consecutive runs of 18 samples each. The following mean sampling durations ±S.D. (ms) were obtained: $51.2\pm1.2$; $51.9\pm1.3$; $50.7\pm1.6$; $52.4\pm2.1$; $52.5\pm1.6$; $51.3\pm1.1$; $51.4\pm1.7$; $52.4\pm1.5$. It thus appears that the standard deviations of these measurements represent a 2.1–4.0% variation around the mean value on a run of 18 samples. However, since the range of variation between the lowest and highest values during single or consecutive runs (49–56 ms in the above measurements) can represent as much as 10–15% of these mean values, the sampling duration times are routinely monitored in our experiments and standardized to a duration time of 50 ms, which corresponds to a 50 μl sampling volume according to the curve shown in FIG. 5.

It is thus clear that such a system allows for fast, multiple, and reproducible sampling from the same mixture with a very small dead time which is actually fixed by the sampling duration (volume). From the above numbers, it can be readily seen that the injection system could operate at a rate of 10 samples per second with a 50 μl sampling volume.

A semiautomatic washing circuit is also connected to the bottom of the chamber. When the valve 68 is closed, this circuit is not connected with the incubation chamber 10 and the three-way valve 60 is opened to the vacuum circuit which is under the control of the vacuum pump 65. The residual medium present in the incubation chamber 10 is aspirated by this vacuum circuit after opening of the valve 68 by manual control. By manual control, the valve 60 can be opened to a flow of deionized water which fills up the chamber 10 by gravity. This sequence can be repeated and a minimum of five consecutive washings were found necessary to properly clean the chamber 10 between assays as estimated from radioactivity measurements after consecutive washings.

The manifold array 70 is formed by a moveable plexiglass block on which are fixed 18 filter holder units. The plexiglass block is fixed on a endless rod which is firmly attached to a stepping motor (not shown). Before each sampling, the motor steps forward to place one filter holder unit directly below the exit 12 of the incubation chamber 10. The motor is controlled by the internal microcomputer of the apparatus and so, the sequence of sampling, filtration, and washings is fully automated and synchronized to a predetermined time sequence. Actually, it is the functioning of this motor which sets the limit of the fast sampling sequence to 4 per second.

Each filter holder unit is composed of an upper reservoir (1.5 ml) which allows for recuperation of the uptake mixture and to which is connected the stop solution circuit. The lower part includes the filter holder 74 per se, which can move up and down, such as to allow easy access for filter installation and removal between runs. An enlarged view of the top part of this filter holder system is shown in FIG. 4. The filter support is screwed on a brass rod 116 which is connected to a syringe piston 112. The movement of the filter holder 74 can thus be controlled through the movement of this syringe piston 112, which is semiautomatically controlled through the holding circuit. A lateral perforation in rod 116 also allows for connection of the filter holder 74 to the filtering circuit through tubing 104. The filter support had to be specially designed. A circular groove 80 had to be engraved on the top of the teflon filter support to maximize the filtering rate. Also, an air entry 82 had to be drilled through the teflon support to ensure complete removal of liquid from below the filters and for drying out of the filters at the end of the last washing step. A Teflon O-ring force inserted into a groove at the bottom of the upper reservoir ensures a very good seal and prevents any loss of liquid during the filtering and the washing steps.

The proper functioning of the filter holder units is diagrammed. The holding circuit, which is responsible for the up and down movement of the 18 filter holders, is shown in FIG. 3. This circuit is split into two parts by means of a three-way valve 124, one branch being connected to the 18 filter holders, while the two other branches are connected to an air pressure supply 138 and a vacuum pump 129, respectively. The air pressure is adjusted to 20 psi by means of a regulator 134 and a manometer 136. When connected to the air pressure system, the three-way valve 124 allows for the air pressure to be applied on each filter holder piston 112 and sets up the working, up position of the filters 76. At the end of a run, the vacuum circuit can be selected by triggering valve 124 to its other position and each piston 112 goes down because of the vacuum suction.

The filtering circuit shown also in FIG. 3 is connected to a vacuum pump 100 and is split into 18 individual lines through a manifold 96 connected to 18 valves 106, such as to allow for independent control of the 18 filter units. Actually, different filtration times can be selected for each unit by controlling the opening time of valve 106. Furthermore, this system also gives the flexibility to determine the number of washing sequences to be performed in each individual filter unit.

The stop solution circuit is diagrammed also in FIG. 3 and is alimented through connection to a bottle 88 containing ice-cold stop solution and placed at a higher level than the apparatus. This solution is thus fed into the circuit by the sole force of gravity. Again, a manifold 86 connected to 18 valves 94 allows for splitting this circuit into 18 individual lines and thus for the washing of only one filter unit at a time. The volume of the washing solution to be delivered to each unit is controlled by the opening time of each valve 94. Obviously, the washing circuit is connected to the filtering circuit, such as to allow for a coordinated sequence of filling and emptying.

This system allows for rapid filtration and washings under conditions lasting just a few seconds. Also, the time required for the first drop of a sampled aliquot to reach the upper reservoir was found to be in the order of 5 ms or less.

The following sequence is thus followed for a run to be complete: i) 18 filters are set in place with forceps in each of the filter holder units and the up position of these units is selected; ii) from 5 to 40 $\mu l$ of vesicles are manually loaded inside a pipette tip and the vesicle-containing tip is introduced into the bottom part of the vesicle injector already screwed on top of the incubation chamber. The upper part of the vesicle injector is then screwed in its bottom part with the piston rearmed and maintained in its up position with the pin; iii) the incubation medium is aspirated inside the chamber; iv) ice-cold stop solution (1 ml) is automatically loaded into the upper chamber of each filter unit after keying in the order to the computer; v) the start signal is keyed in the computer, which starts the magnetic stirrer (106 rpm); vi) the pin is manually removed and the piston allows for the injection of vesicles while triggering the whole sequence to follow; vii) mixing is stopped after 100 ms of injection and the sampling sequence starts according to the predetermined time schedule. At the same time, filtration and washing start in those filter holder units which have already received a sample. viii) At the end of the run, the filter holder units are set in the down position from the computer keyboard and the filters can be removed. The vesicle injector is removed and the washing of the incubation chamber can be performed. With two persons working together, such as to speed up the last two manual parts of this sequence, a run consisting of 9 points over 4.5 seconds can be performed every 5 minutes, approximately.

EXPERIMENTAL RESULTS

The present apparatus can be applied to transport studies using human intestinal brush-border membrane vesicles. Since the transport of organic molecules into (brush-border) membrane vesicles is often performed using a $^{14}C$-labeled substrate and a $^{3}H$-labeled space marker (usually D-mannitol), one should first be certain that the two different isotopes, which also label two different molecules, do behave similarly in terms of the water space occupied by the two molecules. In other words, one should first check for the absence of any preferential binding on the filters of one isotope over the other. Since we were planning to apply the present apparatus in evaluating the kinetic characteristics of D-glucose transport in human intestinal brush-border membrane vesicles, the following series of experiments have been performed using H-D-mannitol and C-D-glucose.

In the absence of vesicles, the incubation chamber was loaded with either $^{3}H$-D-mannitol (1.6 $\mu M$, 1.5 $\mu Ci/50$ $\mu l$ sample) or $^{14}C$-D-glucose (46.4 $\mu M$, 0.6 $\mu Ci/50$ $\mu l$ sample) and a sequence of 18 samplings was performed. In the first run, filtration only was allowed, while in the next runs, an equal but increasing number of extra washings and filtrations was performed (from 1 to 5). The results of this experiment are shown in the first two columns of Table 1. For comparison purposes between the retentions of the two isotopes on the filters, the values have been expressed as picomoles $mM^{-1}$ from a 50 $\mu l$ aliquot. It is readily apparent from these values that both isotopes and molecules behave similarly. Moreover, in spite of a slightly decreased retention of isotopes after two washings as compared to only one, there was in fact no significant difference in filter retention between the 1 and 5 washing situations.

The same experimental protocol was repeated in the presence of 10 mM unlabeled mannitol (Table 1, columns 3 and 4) and the background for the two isotopes was found to be essentially identical to that observed in the first experiment. Actually, the background was even slightly increased over that of the pure isotope situation, a result which can be tentatively attributed to the viscosity change in the solutions. In any case, this experiment demonstrates the absence of any specific binding of $^{3}H$-D-mannitol to the filters as well as the insensitivity of the background in tracer D-glucose concentrations to the presence of high concentrations of D-mannitol. A stable background for both isotopes after a cycle of two washings and filtrations is obtained.

Finally, the same experimental protocol was used again in the presence of freshly prepared human brush-border membrane vesicles to test for any interaction between the space marker and the membranes. In this case, both tracer and 10 mM concentrations of $^{3}H$-D-mannitol were tested (D-glucose was not used in this experiment for obvious reasons since any uptake component might have shown up). As is apparent from Table 1, by comparing the last two columns with the third one, the presence of vesicles did not modify the background of D-mannitol at either concentration of the space marker. These results demonstrate the absence of any specific binding of $^{3}H$-D-mannitol on the brush-border membrane vesicles and again confirm that a stable background is achieved after a cycle of only two washings and filtrations.

These series of experiments thus also justify the routine procedure of one filtration plus two extra washings and filtrations which was adopted in all other experiments with vesicles since this procedure essentially removes 98 to 99% of the two isotopes.

In order to diminish as much as possible the weight of the manifold array and thus the inertia of this moving part of the apparatus, we have chosen to construct this unit under the most compact form and thus to use filters of 12.5 mm diameter instead of the 25 mm ones classically used in the manual application of the filtration technique known in the art. However, it is well known that two major limitations of the filtration technique are: i) the substrate efflux from the vesicles during the washing and filtering steps, which thus require a procedure as fast as possible; and ii) the possible clogging of the filters with too high loads of vesicles, which will also limit the time required for filtration and washings. Obviously, both of these potential problems are minimized when using a higher surface of filtration and a few tests were thus performed in our system to evaluate them.

In order to reduce to a minimum the duration of the filtration/washing step, we have tried filters of different porosity (0.45 and 0.65 μm pore size) from different sources (Millipore (trademark), Sartorius (trademark), and MFS (trademark)). In the presence of vesicles, the total duration of a cycle of one filtration followed by two washings and extra filtrations can be completed in 12 seconds with the 0.65 μm filters, a value which is significantly lower than the 18 seconds obtained with the 0.45 μm ones. No major difference in filtration performance was found between the different brands of filters. The MFS filters, however, were found to be less rigid and less expensive, and thus were chosen as preferable for routine use. Also, since the bigger pore size filters might allow for more vesicles to pass through, we next measured the initial rates of D-glucose uptake at a 50 μM concentration in adult human jejunal brush-border membrane vesicles using MFS filters of the two porosities. The values ±S.D. of regression were $0.049 \pm 0.002$ ($n=8$) and $0.048 \pm 0.006$ ($n=9$) nmoles. $s^{-1}$. mg protein$^{-1}$ for the 0.45 and 0.65 μm filters respectively, thus showing that both types of filters were equivalent in terms of vesicle retention. The 0.65 μm pore size filters were thus adopted on a routine basis for their higher filtration rates.

The precise determination of substrate uptake into (brush-border) membrane vesicles, while dependent on the time required to complete the filtration and washing step, also relies for this same reason on the ability of the stop solution to prevent any further uptake or efflux of labeled substrate from the vesicles during this step. The efficiency of the stopping procedure with the present apparatus was evaluated by following the time course of glucose efflux from actively-loaded human intestinal brush-border membrane vesicles into the stop solution. The vesicles were loaded with D-glucose under $Na^+$-gradient conditions during 56 seconds, a time which corresponds to the peak of the overshoot in glucose accumulation. Then, 7 aliquots were sampled at 0.5 second intervals (mean sampling time of $58.25 \pm 1.5$ seconds) and recuperated into the manifold array, the upper chamber containing 1 ml of isotonic and isosmolar ice-cold stop solution with 1 mM phlorizin and 200 mM NaCl. The sequence of filtrations and washings of the samples was then initiated either immediately or following a delay period of increasing length. As estimated by one way analysis of variance, there was no significant differences in the uptake values for at least the 60 seconds following the dilution of the vesicles into the stop solution. However, using linear regression, the data are compatible with a loss in the vesicle content representing 0.25 nmoles. min$^{-1}$. mg protein$^{-1}$, a quantity which represents a 10% decrease over a 1 minute time interval. Since the conditions chosen for this experiment maximize the gradient in tracer concentration from inside to outside, which constitutes the main driving force for efflux under these conditions, it can be calculated from the regression line that a maximum of 0.05 nmoles. mg protein$^{-1}$ (representing 1.9% of the zero time uptake value) would be lost during the 12 second interval necessary for the routine sequence of filtration and washings with the present apparatus.

Figures 6, 7:
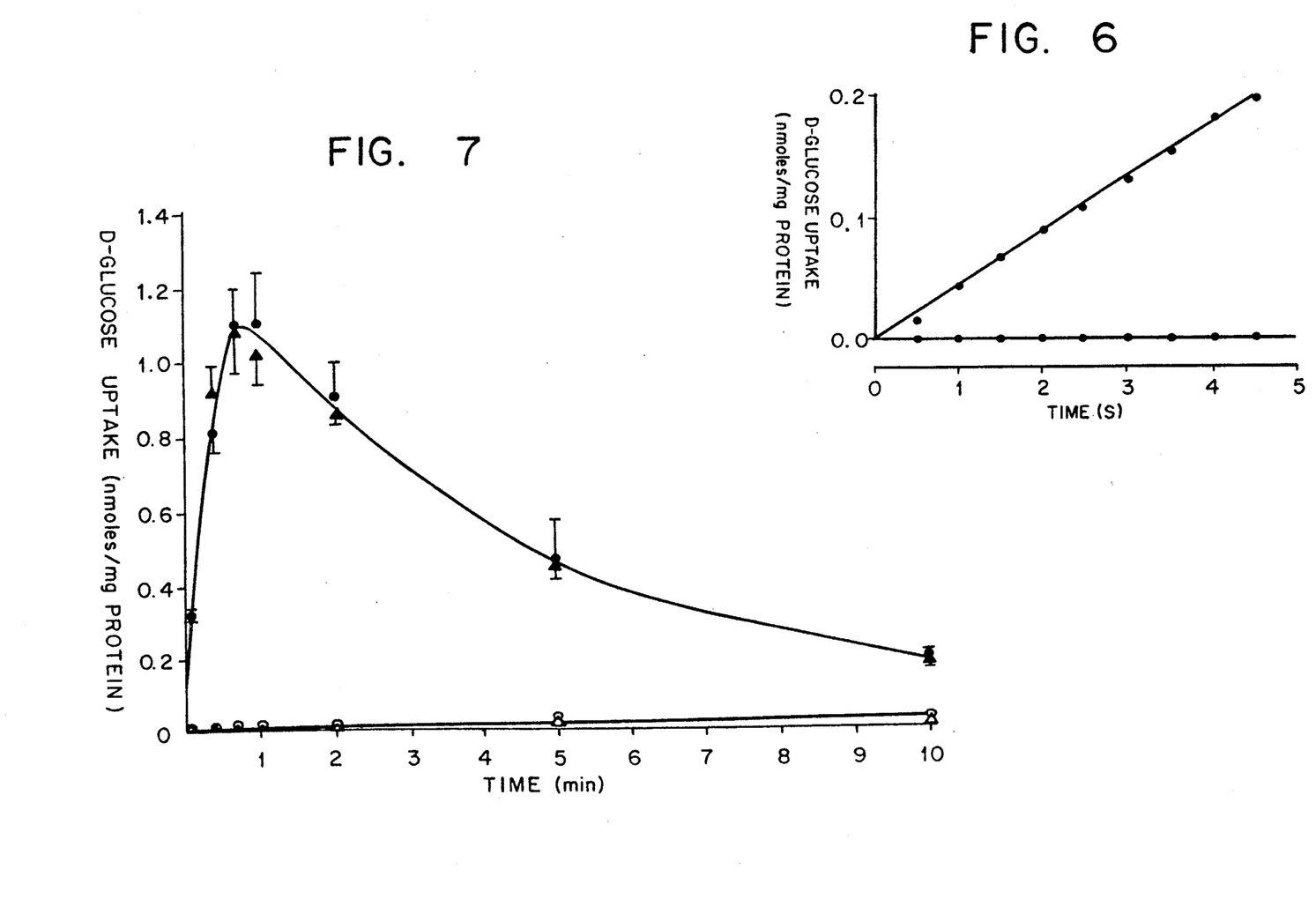
FIG. 6 illustrates concentration of D-glucose with respect to time, in seconds.
FIG. 7 is a diagram illustrating concentration of D-glucose with respect to time, in minutes.

FIGS. 6 and 7 show the 10 minutes time course of 50 μM $^{14}$C-D-glucose uptake into human intestinal brush-border membrane vesicles using either the manual rapid filtration technique or its fully automated version as allowed by the present apparatus. It clearly appears from FIG. 7 that similar uptake-time courses are obtained by the two techniques when measuring transport under $Na^+$-gradient conditions in the presence or absence of phlorizin. The data of FIGS. 6 and 7 also show that D-glucose uptake in adult human jejunal brush-border membrane vesicles is a transient, $Na^+$-dependent and phlorizin-sensitive phenomenon, thus confirming previous studies using the same preparation. It can also be noted from FIGS. 6 and 7 that the peak of the overshoot in $Na^+$ D-glucose cotransport appears around 1 min under the conditions of this experiment.

A small difference in the protocols used for comparing the manual and the present invention approaches deserves some comment. As is usually done for the manual application of the technique, the radiolabeled space marker $^3$H-D-mannitol was added to the stop solution in the case of the manual uptake. However, in order to avoid contamination by radiotracer in the washing circuit of the manifold array, the vesicles were coincubated with both the space marker and the radioactive substrate in the incubation chamber when working with the present apparatus. Since the space-corrected D-glucose uptake values were found to be identical with the two techniques, one has to infer that D-mannitol does not significantly enter into the vesicles, at least over the 10 minutes time interval studied. This point has been evaluated directly by plotting $^3$H-D-mannitol uptake as a function of time. The slope of this uptake-time curve, as analyzed by linear regression analysis, was found to represent $2.35 \cdot 10^{-4} \pm 1.69 \cdot 10^{-4}$ picomoles $s^{-1}$. mg protein$^{-1}$. Accordingly, $0.141 \pm 0.101$ picomoles of D-mannitol. mg protein$^{-1}$ would have entered the vesicles after a 10 minutes incubation period, a value which represents only 0.23% of the D-glucose content measured at the same time point.

Obviously, the results of FIGS. 6 and 7 demonstrate that the present apparatus can indeed reproduce very faithfully the manual aspects of the rapid filtration technique. However, it should be noted that the present apparatus was not designed to analyze uptake time courses over long time periods but, on the contrary, over their very early time points. Indeed, the particularly significant advantage of the present approach over the manual approach is clearly exemplified in the inset of FIG. 6 where 9 points have been recorded over the first 4.5 seconds of uptake. For comparison, it should be mentioned that our manual set up does allow for a maximum of only 2 time points over a time period of 5 seconds from the same incubation medium. Thus, the initial rates of D-glucose uptake can be followed under real time conditions and estimated by linear (or non-linear, should the early time points not follow a straight line) regression analysis. For example, under the experimental conditions of FIGS. 6 and 7, a linear regression analysis of the uptake-time curve shown in the inset gave y intercept, slope and correlation coefficient of $-2.6 \cdot 10^{-3} \pm 2.4 \cdot 10^{-3}$ nmoles. mg protein$^{-1}$, $0.045 \pm 0.001$ nmoles $s^{-1}$. mg protein$^{-1}$ and 0.999, respectively.

In FIGS. 6 and 7, for both assays, human jejunal brush-border membrane vesicles were resuspended in 50 mM Tris-Hepes buffer (pH 7.5), 0.1 mM MgSO$_4$, 100 mM KCl, 200 mM choline chloride, 125 mM mannitol and 5 μM valinomycin. The final concentrations in the incubation media were: 50 mM Tris-Hepes buffer (pH 7.5), 0.1 mM MgSO$_4$, 100 mM KCl, 192 mM NaCl, 8 mM choline chloride, 125 mM mannitol, 0.5 mM amiloride, 50 μM $^{14}$C-D-glucose and 1.3 mM $^3$H-D-mannitol. $^3$H-D-mannitol was added to either the stop solution or the incubation medium for the manual (▲, Δ) and automated (●, 0) assays, respectively. Transport was assayed under both conditions in the absence (▲, ●) or presence (Δ, 0) of 1 mM phlorizin. Points shown are the mean ±S.D. from three determinations. A typical short time uptake as obtained with the fast sampling, rapid filtration apparatus is shown in the inset.

TABLE I

Binding of $^3$H and $^{14}$C Isotopes on Both Filters and Vesicles

| | Without vesicles | | | | With vesicles | |
|---|---|---|---|---|---|---|
| | | | 10 mM unlabeled mannitol | | | 10 mM unlabeled mannitol |
| Washings | $^3$H-D-Mannitol | $^{14}$C-D-glucose | $^3$H-D-mannitol | $^{14}$C-D-glucose | $^3$H-D-mannitol | $^3$H-D-mannitol |
| 0 | 243.0 ± 60.5[1] | 288.8 ± 79.4 | 304.4 ± 76.2 | 269.5 ± 82.8 | 274.4 ± 71.2 | 229.2 ± 71.6 |
| 1 | 9.7 ± 5.4 (4.0%)[2] | 8.6 ± 5.6 (3.0%) | 12.9 ± 5.9 (4.2%) | 14.1 ± 5.5 (5.2%) | 13.8 ± 5.6 (5.0%) | 14.0 ± 6.1 (6.1%) |
| 2 | 2.6 ± 1.8 (1.1%) | 2.1 ± 1.9 (0.7%) | 5.4 ± 3.7 (1.8%) | 6.0 ± 2.3 (2.2%) | 5.2 ± 3.6 (1.9%) | 6.0 ± 5.4 (2.6%) |
| 3 | 2.5 ± 2.1 (1.0%) | 2.9 ± 2.6 (1.0%) | 4.4 ± 2.4 (1.4%) | 5.8 ± 2.3 (2.2.%) | 4.3 ± 2.4 (1.6%) | 7.0 ± 3.7 (3.1%) |
| 4 | 3.8 ± 2.4 (1.6%) | 2.3 ± 2.1 (0.8%) | 5.1 ± 2.5 (1.7%) | 6.1 ± 1.9 (2.3%) | 5.1 ± 2.5 (1.9%) | 5.4 ± 3.8 (2.4%) |
| 5 | 3.0 ± 2.2 (1.2%) | 2.3 ± 2.2 (0.8%) | 2.7 ± 2.0 (0.9%) | 6.0 ± 2.4 (2.2%) | 2.8 ± 2.0 (1.0%) | 4.7 ± 2.9 (2.1%) |

[1] Mean ± SD from 18 determinations. Results are expressed as pmoles. mM$^{-1}$
[2] % of residual substrate.

Although the present invention has been explained hereinabove by way of a preferred embodiment thereof, it should be pointed out that any modifications to this preferred embodiment, within the scope of the appended claims is not deemed to change or alter the nature and scope of the present invention.

The embodiments of the invention in which an exclusive property or privilege is claimed are defined as follows:

1. An electropneumatic apparatus for performing a fast sampling of a liquid mixture, comprising:
   a chamber for containing said mixture, said chamber having a bottom aperture provided with a flow sensor connected to a processing and controlling means, and an upper aperture;
   a pressurized air system connected to said upper aperture and capable of alternately producing inside said chamber positive and negative pressures relative to an ambient pressure existing outside said chamber, said liquid mixture being held inside said chamber by said negative pressure produced by said air system, said air system being controlled by said processing and controlling means; and
   a manifold array under said bottom outlet for collecting predetermined sample volumes of said liquid mixture, said manifold array being movable by means of a motor controlled by said processing and controlling means;
   whereby a succession of said negative and positive pressures inside said chamber are producible by means of said pressurized air system controlled by said processing and controlling means, for exiting said predetermined sample volumes from said bottom aperture, said processing and controlling means calculating said predetermined sample volumes by means of said flow sensor, and said manifold array collecting said predetermined sample volumes.

2. An apparatus according to claim 1, further comprising:
   an injector having an outlet for injecting a first reagent into said chamber, said injector being provided with a detector connected to said processing and controlling means for indicating activation of said injector;
   and wherein:
   said chamber is included in a reactor, said chamber being provided with an inlet detachably connected to said outlet of the injector for receiving the first reagent from said injector such that said first reagent is mixed with a second reagent already inside said chamber for producing said mixture, said flow sensor indicating a volume of fluid exiting from said bottom aperture;
   said pressurized air system has an air channel provided with a first portion connectable to an air source, and a second portion connected to the upper aperture of said chamber, said air channel being provided with air controlling means connected to said processing and controlling means for producing said succession of positive and negative pressures inside said chamber; and
   said manifold array is included in a receiving system for receiving successive samples of said mixtures exiting from the bottom aperture of said chamber;
   whereby, once said first reagent is injected into said chamber and said mixture is obtained as desired, said predetermined volumes of said mixture are sampled from said bottom aperture under control of said processing and controlling means.

3. An apparatus according to claim 2, wherein said injector further comprises:
   a pipet holder mounted on top of said reactor, for holding a pipet containing said first reagent;
   a rod having an end removably inserted into said pipet for ejecting said first reagent out of said pipet by driving said rod into said pipet;
   a piston device to be mounted on top of said pipet holder, said piston device including a piston cylinder, a piston disposed inside said cylinder and a return spring for biassing said piston toward said rod; and
   a pin for locking said piston in a position where said return spring is compressed;

whereby a user activates said injector to eject said first reagent out of said pipet into said reactor by removing said pin.

4. An apparatus according to claim 2, wherein said reactor further comprises:
- a first channel having inlet and outlet connected to a thermoregulating system controlled by said processing and controlling means, whereby a thermoregulating fluid is injected into said first channel for regulating the temperature of said mixture in the chamber;
- a probe disposed in a bottom portion of said chamber and connected to said processing and controlling means for monitoring the temperature of said mixture in the chamber;
- a second channel linking the bottom portion of said chamber to inlet/outlet means of said reactor, connected to a washing system for alternately entering and exiting a washing fluid to and from said chamber;

and wherein said chamber is cruciform.

5. An apparatus according to claim 4, wherein said washing system comprises:
- a first three-way valve controlled by said processing and controlling means, said three-way valve having an inlet connectable to a washing fluid source, an outlet connectable to a vacuum means, and inlet/outlet means, said inlet and said outlet being respectively closed and open when said three-way valve is not activated; and
- a second valve controlled by said processing and controlling means, said second valve having first inlet/outlet means connected to the inlet/outlet means of said first valve, and second inlet/outlet means connected to the inlet/outlet means of said reactor;

whereby a washing fluid is sent into said chamber when said first and second valves are activated, a fluid inside said chamber is sucked by means of said vacuum means when only said second valve is activated, and no washing operation is performed on said chamber when said first and second valves are not activated.

6. An apparatus according to claim 2, wherein the second portion of said air channel has a reduced diameter with respect to a diameter of the first portion of said air channel, and said air controlling means comprise:
- a first manual regulating valve disposed along the first portion of said air channel;
- a venturi having an inlet connected to the first portion of said air channel, an inlet/outlet middle aperture connected to the second portion of said air channel, and an outlet;
- a first impulsion valve controlled by said processing and controlling means, having an end connected to the outlet of said venturi;
- a second impulsion valve controlled by said processing and controlling means, having an end connected to another end of said first impulsion valve and another end connected to ambient atmosphere;
- a second manual regulating valve connected in parallel to said second impulsion valve; and
- a manometer disposed along the first portion of said air channel;

whereby said first manual valve is used by a user for regulating air pressure inside said air channel, said second manual valve is used by the user for producing said negative pressure inside said chamber, said first impulsion valve is controlled by said processing and controlling means for producing said succession of negative and positive pressures inside said chamber by which said first sampling of the predetermined volumes is done, and said second impulsion valve is controlled by said processing and controlling means for producing said negative pressure inside said chamber during a certain time period after that said positive pressure is produced inside said chamber to reestablish as fast as possible said negative pressure inside said chamber.

7. An apparatus according to claim 1, wherein said manifold array further comprises:
- an array of reservoirs for receiving each of said predetermined volumes of said mixture from the bottom aperture of said chamber;
- a filter holder system having a plurality of holding members forming respectively the bottom of each of said reservoirs for holding filters, each of said holding members having a filter seat provided with a concentric groove for increasing filtering rate, and a channel outlet for draining liquid from said mixture passing through a corresponding one of said filters.

8. An apparatus according to claim 7, wherein said receiving system further comprises:
- a stop solution system having a manifold array provided with an inlet connected to a stop solution source, and a plurality of outlets connected to corresponding tubes having each a valve controlled by said processing and controlling means, said tubes being connected to corresponding reservoirs of said mobile manifold array; and
- a collecting system having a manifold array provided with an outlet connected to a vacuum means, and a plurality of inlets connected to corresponding tubes having each a valve controlled by said processing and controlling means, said tubes of said collecting system being connected respectively to said channel outlets of said holding members of said filter holder system;

and wherein each of said holding members further has an air admission channel connecting the corresponding groove to an outside of the corresponding holding member.

9. An apparatus according to claim 8, further comprising pneumatic means having:
- piston cylinder assemblies for containing each of said holding members, each of said assemblies having a piston and a cylinder into which said piston is slideably mounted, each of said piston cylinder assemblies having a channel providing a passageway for the corresponding tubing of the collecting system, each of said piston having an upper portion connected to the corresponding holding member and an airtight lower portion slideably mounted into the corresponding cylinder, each of said cylinders having a side aperture for positioning a filter on the corresponding holding member when its corresponding piston is down, and a bottom aperture;
- a tubing connected to the bottom aperture of each of said cylinders;
- and a three-way valve controlled by said processing and controlling means, said three-way valve having an inlet connected to said tubing, a vacuum outlet connected to vacuum means, and an air pressure outlet connected to a pressurized air channel provided with a regulator and a manometer, and being connected to a pressurized air source, said vacuum outlet and said air pressure outlet being respectively open and closed when said three-way valve is not activated, whereby said tubing of said pneumatic means is linked to said vacuum means, to bring the pistons down when said three-way valve is not activated by said processing and controlling device, and said tubing of said pneumatic means is linked to said pressurized air source to lift the pistons in operative position when said three-way valve is activated by said processing and controlling means.

* * * * *